(12) United States Patent
Scorese et al.

(10) Patent No.: US 12,350,363 B2
(45) Date of Patent: Jul. 8, 2025

(54) COSMETIC COMPOSITION FOR EYELASHES

(71) Applicant: L'ORÉAL, Paris (FR)

(72) Inventors: Alison Jeanne Scorese, Garwood, NJ (US); Aline Aude Guimont, Sourth Orange, NJ (US)

(73) Assignee: L'ORÉAL, Paris (FR)

( * ) Notice: Subject to any disclaimer, the term of this patent is extended or adjusted under 35 U.S.C. 154(b) by 78 days.

(21) Appl. No.: 16/286,919

(22) Filed: Feb. 27, 2019

(65) Prior Publication Data

US 2020/0268640 A1   Aug. 27, 2020

(51) Int. Cl.
*A61K 8/92* (2006.01)
*A61K 8/81* (2006.01)
*A61Q 5/00* (2006.01)

(52) U.S. Cl.
CPC ............ *A61K 8/922* (2013.01); *A61K 8/8117* (2013.01); *A61K 8/8147* (2013.01); *A61Q 5/002* (2013.01)

(58) Field of Classification Search
None
See application file for complete search history.

(56) References Cited

U.S. PATENT DOCUMENTS

| | | | |
|---|---|---|---|
| 8,920,787 B2 * | 12/2014 | Li | A61K 8/8152 |
| | | | 424/70.7 |
| 9,216,303 B2 * | 12/2015 | Norman | A61K 8/37 |
| 2005/0130991 A1 * | 6/2005 | Dalko | A61K 8/4953 |
| | | | 544/326 |
| 2012/0107256 A1 * | 5/2012 | Delvalle | A61K 8/891 |
| | | | 424/59 |
| 2013/0164241 A1 * | 6/2013 | Foley | A61K 8/8141 |
| | | | 424/70.7 |

FOREIGN PATENT DOCUMENTS

| | | | |
|---|---|---|---|
| KR | 101060849 B1 | 8/2011 | |
| KR | 101384488 B1 | 4/2014 | |
| WO | WO-2004058162 A2 * | 7/2004 | ............ A61K 8/26 |

OTHER PUBLICATIONS

"L'Oreal Volume Shocking", Mintel GNPD, record ID 510749, published Mar. 2006, pp. 1-2.
"Lash Maximizer Essence", Kanebo Cosmetics, www.kanebo-cosmetics.jp/products/en/2031792/, published Jan. 2006, retrieved May 6, 2019, pp. 1-3.

* cited by examiner

*Primary Examiner* — David J Blanchard
*Assistant Examiner* — Sarah J Chickos
(74) *Attorney, Agent, or Firm* — MEAGHER EMANUEL LAKS GOLDBERG & LIAO. LLP

(57) ABSTRACT

Disclosed is an unpigmented cosmetic composition for treatment of keratin materials, which includes at least one cosmetic butter and at least one styrenic film former. Also disclosed are methods of use for the unpigmented cosmetic composition, either as by itself, or as a primer for a pigmented cosmetic composition.

11 Claims, 2 Drawing Sheets

COSMETIC COMPOSITION FOR EYELASHES

FIELD OF THE INVENTION

The present invention relates to a cosmetic composition for eyelashes, and specifically to lash masks. The present invention also relates to a cosmetic process for enhancing eyelashes by using the cosmetic composition.

BACKGROUND

A multitude of cosmetic compositions are focused on shaping (including lengthening, thickening, curling) and/or coloring eyelashes and eyebrows. Various approaches for increasing the durability of such treatments or color are utilized, to the point where harsher and harsher removal techniques are needed when such treatments or coloring are no longer desired. The daily exposure to such physical stresses, as well as ordinary environmental stresses, can damage eyelashes and eyebrows.

Efforts to modify existing formulas to condition eyelashes during wear poses a technical challenge, as high loads of conditioning agents (such as butters or waxes) typically interfere with the other required performance characteristics (e.g., ease of deposition, build-up, evenness of the coating, etc.) of the mascara or other cosmetic composition.

As such, a readily deposited composition for perceivably conditioning eyelashes or making it easier to remove compositions such as mascaras, without substantially impacting other performance characteristics, is therefore desirable.

BRIEF SUMMARY

Disclosed is an unpigmented cosmetic composition for perceivably conditioning of keratin materials, which includes at least one cosmetic butter and at least one styrenic film former. In various embodiments, the composition may include natural origin butters, two or more butters, and the butters may include or consist of shea, mango, cocoa and/or jojoba butters, which may be present in the composition at an amount of between 10 and 40% by weight. In various embodiments, the film former may be a latex copolymer, and may be present in the composition at an amount of between 5 and 10% (on an active basis) by weight.

In certain embodiments, the unpigmented cosmetic composition is configured such that the shear viscosity, when measured at a shear rate of $0.12\ s^{-1}$ and at 25° C., is less than 1500 Pa-s after being held at room temperature (25° C.±5° C.) for three months. In certain embodiments, the unpigmented cosmetic composition is configured such that the complex modulus of the composition, at an oscillation strain of 0.1%, is less than 15,000 Pa after being held at room temperature (25° C.±5° C.) for two months.

Also disclosed is a method for the treatment of keratin materials, by applying the unpigmented cosmetic composition to a keratin material, such as an eyelash, and allowing it to remain in contact with the keratin material for a period of time, which may be between 5 minutes and 24 hours, or overnight, after which the composition can be removed.

Also disclosed is a method for priming a keratin material, such as an eyelash, for pigmentation. This is done by applying the unpigmented cosmetic composition to a keratin material, then applying a pigmented cosmetic composition to the keratin material, on top of the unpigmented cosmetic composition. These two compositions are allowed to remain in contact with the keratin material for a period of time, which may be between 5 minutes and 24 hours, or overnight, after which the two compositions can be removed.

DETAILED DESCRIPTION

Figure 1:
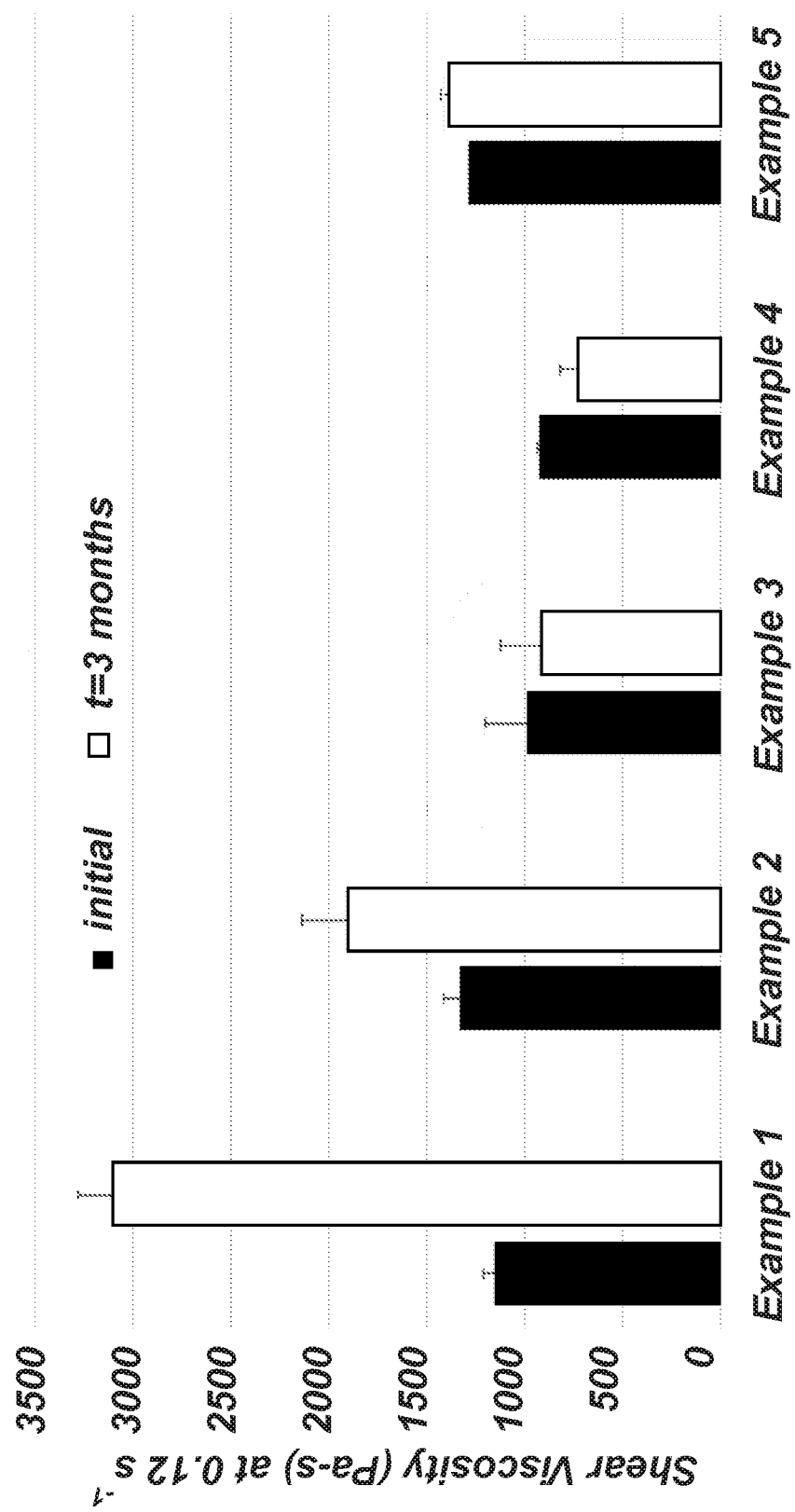
FIG. 1 is a graph of low-shear viscosity measurements at two different points in time for several example formulations.

As used herein, articles such as "a" and "an" when used in a claim, are understood to mean one or more of what is claimed or described.

As used herein, the expression "at least one" means one or more and thus includes individual components as well as mixtures/combinations.

All percentages listed are by weight unless otherwise noted.

As used herein, the term "about [a number]" is intended to include values rounded to the appropriate significant digit. Thus, "about 1" would be intended to include values between 0.5 and 1.5, whereas "about 1.0" would be intended to include values between 0.95 and 1.05.

As used herein, the terms "include", "includes" and "including" are meant to be non-limiting.

As used herein, "substituted" means comprising at least one substituent. Non-limiting examples of substituents for substitution include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

As used herein, "pigmented" compositions are those containing a cosmetically effective load of at least one pigment. Typically, cosmetically effective loads are those containing at least 1.0% by weight of the at least one pigment. Typically, pigments are inorganic. Examples of inorganic pigments include, but are not limited to, talc, mica, magnesium carbonate, calcium carbonate, magnesium silicate, aluminum magnesium silicate, silica, titanium dioxide, zinc oxide, red iron oxide, yellow iron oxide, black iron oxide, ultramarine, polyethylene powder, methacrylate powder, polystyrene powder, silk powder, crystalline cellulose, starch, titanated mica, iron oxide titanated mica, bismuth oxychloride, and the like. Examples of organic pigments include, but are not limited to, carbon black, and barium, strontium, calcium and aluminum lakes. The aforementioned pigments can be used independently or in combination.

As used herein, "unpigmented" compositions are those that do not contain cosmetically effective loads of at least one pigment.

The present invention is drawn to a cosmetic composition and specifically to unpigmented cosmetic compositions utilizing at least one cosmetic butter and at least one styrenic film former.

The cosmetic composition includes at least one cosmetic butter, and preferably includes natural origin butters, and preferably plant-based natural origin butters, including but not limited to Butyrospermum Parkii (Shea) Butter, Mangifera Indica (Mango) Seed Butter, Simmondsia Chinensis (Jojoba) Butter, and Theobroma Cacao (Cocoa) Seed Butter.

In one preferred embodiment, the only butter used is jojoba butter. In another preferred embodiment, shea, mango, jojoba, and cocoa butter are utilized.

The at least one cosmetic butter should be present in the formula in a total amount of between about 10% and about 40% by weight. In preferred embodiments, the total amount of butter is between about 12% and about 20%, and more preferably between about 14% and about 18%.

The unpigmented cosmetic composition also includes at least one styrenic film former. Suitable film formers may include homopolymers, copolymers, and block and graft copolymers comprised of repeating substituted and/or unsubstituted styrene monomers.

The styrenic film former may be a latex film former, such as a latex copolymer. Such latex film formers include, but are not limited to, random styrene acrylate copolymers and derivatives thereof.

The styrenic film former may have a thermoplastic resin with a molecular weight (in g/mol) that will vary considerably depending upon its characteristics including its cross-linking, but generally will range from about 10,000 to greater than 1,000,000 (up to about 10,000,000 or more), from about 25,000 to about 1,000,000, about 50,000 to about 1,000,000, about 100,000 to about 750,000, and about 150,000 to about 500,000.

In certain embodiments, the styrenic film former may be dispersed at 10%-60% polymer by weight in water.

In certain embodiments, a random styrene acrylate copolymer and derivatives thereof may be chosen from those having a glass transition temperature ($T_g$) ranging from about −15° C. to about 90° C., such as from about 0° C. to about 50° C.

In certain embodiments, the styrenic film former may be selected from styrene/acrylates/ammonium methacrylate copolymers, styrene-acrylates copolymers, and/or styrene acrylic copolymers. Exemplary commercial styrenic film formers that may be used include, but are not limited to, those sold under the SYNTRAN® trade name by Interpolymer Corporation; those sold under the JONCRYL® trade name by BASF Performance Chemicals; and those sold under the RHOPLEX® trade name by Dow Chemical Company.

In certain embodiments, the at least one styrenic film former may be present in the cosmetic composition in an amount ranging from about 1% to about 10%, and more preferably from about 5% to about 10%, and still more preferably from about 6% to about 9%. These percentages refer to the amount of active film former in the composition. As is understood by those of skill in the art, some film formers are provided in a dispersion, such as an aqueous dispersion, where only a percentage of the dispersion is the active ingredient qualifying as a film former.

Other cosmetically acceptable materials may also be present in the composition. For example, water, preservatives, emollients, emulsifiers, surfactants, rheology modifiers, antioxidants, and/or fragrances may also be included.

In certain embodiments, the unpigmented cosmetic composition may be designed such that the shear viscosity of the composition measured at 25° C. at a shear rate of 0.12 $s^{-1}$ is less than 1500 Pa-s after being held at room temperature (25° C.±5° C.) for three months. The shear viscosity was obtained using a flow ramp from 0.1 to 100 $s^{-1}$ in 240 s, using a cone/plate viscometer (such as a Discovery HR-2 rheometer or the like). In certain embodiments, this viscosity has no statistically significant (p<0.005) change from time t=0 to time t=3 months.

Example Formulas

| Formula # | 1 | 2 | 3 | 4 | 5 |
|---|---|---|---|---|---|
| Cocoa Butter | 16.5% | — | — | — | 3.83% |
| Mango Butter | — | 16.5% | — | — | 3.83% |
| Jojoba Butter | — | — | 16.5% | — | 3.84% |
| Shea Butter | — | — | — | 16.5% | 5% |
| Film Former + Other | 83.5% | 83.5% | 83.5% | 83.5% | 83.5% |

Each example formula was produced by combining the materials, except for the film formers, at room temperature, then melting together at 80-85° C. until uniform. The formulas were then cooled to 60° C., followed by addition of the film formers and mixing until uniform while cooling to room temperature.

Referring to FIG. 1, the low-shear viscosities of Example Formulas 1-5 can be seen at the initial time t=0 (black bars) and time t=3 months (white bars). As can be seen, there is no statistically significant (p<0.005) change over time for either Example Formula 3 or Example Formula 5. Further, while all formulas have a low-shear viscosity of less than 1500 Pa-s at 0.12 $s^{-1}$ initially, Examples 3, 4, and 5 have low-shear viscosities of less than 1,500 Pa-s at 0.12 $s^{-1}$ after three months.

In certain embodiments, the unpigmented cosmetic composition may be designed such that the complex modulus (G*) of the composition in the viscoelastic region, such as at a strain of 0.1%, is less than 15,000 Pa after being held at room temperature (25° C.±5° C.) for two months. Complex modulus was determined from a strain sweep at 20° C. using, e.g., a TA Instruments Discovery HR-2 rheometer, and a 40 mm stainless steel 2° cone, with no preshear, and 60 second equilibration time, from 0.01 to 1000% strain at 1 rad/sec angular frequency. In preferred embodiments, G* is less than 10,000 Pa after being held at room temperature (25° C.±5° C.) for two months.

Figure 2:
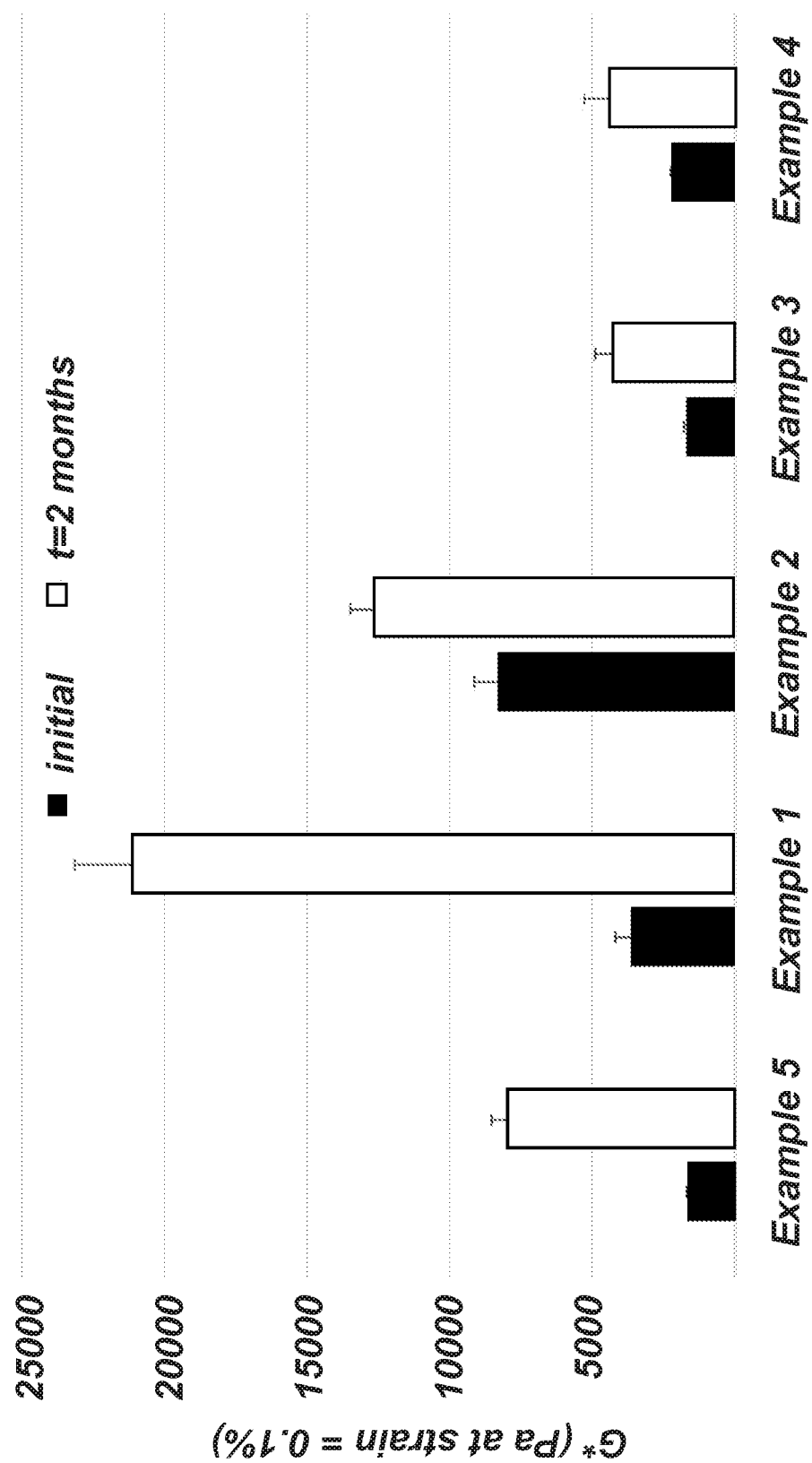
FIG. 2 is a graph of complex modulus measurements at two different points in time for several example formulations.

Referring to FIG. 2, the complex modulus (G*) of Example Formulas 1-5, at a strain of 0.1%, can be seen at the initial time t=0 (black bars) and time t=2 months (white bars). As can be seen, there is statistically significant (p<0.005) change over time for all formulas. Further, while all formulas have a G* of less than 15,000 Pa at 0.1% strain initially, Examples 2, 3, 4, and 5 have a G* of less than 15,000 Pa at 0.1% strain after two months, Examples 3, 4 and 5 have a G* of less than 10,000 Pa, and Examples 3 and 4 may have a G* of less than 5,000 Pa.

In some embodiments, there may be an increased deposition weight and/or eyelash surface area as compared to related, traditional cosmetic formulations. In one example, both the average deposition weight and eyelash surface area increased significantly over an unpigmented version of a commercially available product.

| Product | Average Deposition (g/lash) [Std Dev] | Average Increase In Surface Area ($mm^2$) [Std Dev] |
|---|---|---|
| Example Formula 5 | 0.0120 [0.0006] | 32.55 [4.89] |
| Unpigmented Version of a Commercially Available Product | 0.0074 [0.0007] | 18.44 [5.12] |

In some embodiments, there may be an increased deposition weight and/or eyelash surface area as compared to related, traditional cosmetic formulations. In one example, both the average deposition weight and eyelash surface area increased significantly over an unpigmented version of a commercially available product. Average deposition was determined by weighing a synthetic eyelash before and after an application comprised of two sets of 15 strokes of the product, repeating ten times, and taking an average. Surface area was determined using a camera and appropriate imaging software.

Also disclosed are methods for utilizing these unpigmented compositions. In one embodiment, a method for treating keratin materials is disclosed. In this method, the unpigmented cosmetic composition is first applied to a keratin material (e.g., eyelashes, eyebrows, etc.) and then allowed to remain in contact with the keratin material. In some embodiments, the unpigmented cosmetic composition may remain on the keratin material for between 5 minutes and 24 hours, and in certain embodiments, for between 30 minutes and 8 hours. This may include time when the subject on which the composition has been applied is awake and/or asleep, such as when the composition is applied before bedtime, then left on overnight. The composition may then be readily removed, and the keratin material may be perceived to have been conditioned.

In some embodiments, there may be an increased deposition weight and/or eyelash surface area as compared to related, traditional cosmetic formulations.

In one example, both the average deposition weight and eyelash surface area increased significantly over a unpigmented version of a commercially available product.

In another embodiment, a method for using the unpigmented composition as a primer for a pigmented composition is disclosed. In this method, the unpigmented cosmetic composition is first applied to a keratin material to act as a primer. At a later point in time, a pigmented cosmetic composition is then applied over the unpigmented cosmetic composition. The combined compositions—the unpigmented under the pigmented cosmetic composition—may sometimes be allowed to remain on the keratin material for between 5 minutes and 24 hours, and in certain embodiments, for between 4 hours and 126 hours. The two compositions may then be readily removed.

Those skilled in the art will recognize or be able to ascertain using no more than routine experimentation many equivalents to the specific embodiments of the invention described herein. Such equivalents are intended to be encompassed by the following claims.

What is claimed is:

1. A method for the cosmetic treatment of keratin materials, comprising the steps of:
    applying an unpigmented cosmetic primer composition to a keratin material, the unpigmented cosmetic composition consisting of:
        water;
        an emulsifier;
        at least one cosmetic butter in an amount of between 10% and 40% by weight of the unpigmented composition, the at least one cosmetic butter consisting of shea, mango, cocoa and jojoba butters;
        at least one styrenic film former; and
        one or more additional materials consisting of a preservative, an emollient, an emulsifier, a surfactant, a rheology modifier, an antioxidant and/or a fragrance; and
    allowing the unpigmented cosmetic primer composition to remain in contact with the keratin material overnight to provide a cosmetic treatment to the keratin material.

2. The method according to claim 1, further comprising removing the unpigmented cosmetic composition.

3. The method according to claim 1, wherein the keratin material is an eyelash.

4. The method according to claim 1, wherein the at least one styrenic film former is present in an amount between 5% and 10% by weight of the unpigmented cosmetic primer composition.

5. The method according to claim 1, wherein the unpigmented cosmetic primer composition has a shear viscosity measured at 25° C. at a shear rate of 0.12 $s^{-1}$ that is less than 1500 Pa-s after being held at 25° C. ±5° C. for three months.

6. The method according to claim 1, wherein the styrenic film former is a styrene/acrylates/ammonium methacrylate copolymer, a styrene-acrylates copolymer, a styrene acrylic copolymer, or a combination thereof.

7. A method for providing a cosmetic treatment and priming keratin materials for pigmentation, comprising the steps of:
    applying an unpigmented cosmetic primer composition to a keratin material to provide a cosmetic treatment to the keratin material, the unpigmented cosmetic composition consisting of:
        water;
        an emulsifier;
        at least one cosmetic butter in an amount of between 10% and 40% by weight of the unpigmented composition, the at least one cosmetic butter consisting of shea, mango, cocoa and jojoba butters;
        at least one styrenic film former; and
        one or more additional materials consisting of a preservative, an emollient, an emulsifier, a surfactant, a rheology modifier, an antioxidant and/or a fragrance; and
    applying a pigmented cosmetic composition to the keratin material, on top of the unpigmented cosmetic composition.

8. The method according to claim 7, further comprising allowing the combined unpigmented cosmetic primer composition and pigmented cosmetic composition to remain on the keratin material for between 5 minutes and 24 hours.

9. The method according to claim 7, further comprising removing both the unpigmented cosmetic primer composition and the pigmented cosmetic composition.

10. The method according to claim 7, wherein the at least one styrenic film former is present in an amount between 5% and 10% by weight of the unpigmented cosmetic primer composition.

11. The method according to claim 7, wherein the unpigmented cosmetic primer composition has a shear viscosity measured at 25° C. at a shear rate of 0.12 $s^{-1}$ that is less than 1500 Pa-s after being held at 25° C. ±5° C. for three months.

* * * * *